US006350601B1

(12) United States Patent
Aoki et al.

(10) Patent No.: US 6,350,601 B1
(45) Date of Patent: *Feb. 26, 2002

(54) ENZYME COMPOSITION FOR USE AS A CLINICAL DIAGNOSTIC REAGENT

(75) Inventors: Ryoji Aoki, Tagata-gun; Shigeru Ueda, Nerima-ku, both of (JP)

(73) Assignee: Asahi Kasei Kogyo Kabushiki Kaisha, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,833

(22) PCT Filed: Nov. 10, 1995

(86) PCT No.: PCT/JP95/02303

§ 371 Date: May 8, 1997

§ 102(e) Date: May 8, 1997

(87) PCT Pub. No.: WO96/15256

PCT Pub. Date: May 23, 1996

(30) Foreign Application Priority Data

Nov. 11, 1994 (JP) .............................. 6-277617

(51) Int. Cl.$^7$ .............................. C12N 9/96; C12N 9/00
(52) U.S. Cl. .......................... 435/188; 435/15; 435/17; 435/18; 435/21; 435/25; 435/26; 435/183; 435/196; 435/194; 435/193; 435/190; 435/212; 436/8; 436/15; 436/16; 436/18; 530/350; 530/362; 530/363; 424/94.5; 424/94.6; 424/94.64; 424/94.63
(58) Field of Search .............................. 435/15, 17, 18, 435/212, 21, 190, 25, 193, 26, 188, 196; 436/8, 15, 16, 18; 530/350, 362, 363; 429/94.5, 94.6, 94.64, 94.63

(56) References Cited

U.S. PATENT DOCUMENTS

| 4,325,832 A | 4/1982 | Louderback et al. ........ 252/408 |
| 4,943,530 A | 7/1990 | Christner et al. ............ 435/188 |
| 4,959,179 A | 9/1990 | Aronson et al. ............ 252/135 |
| 5,217,890 A | 6/1993 | Daggett ...................... 435/188 |
| 5,298,406 A | 3/1994 | Loyd et al. .................... 435/17 |
| 5,547,873 A | * 8/1996 | Magneson .................... 436/18 |

OTHER PUBLICATIONS

Peters et al. Kits for Enzyme Determination Compared: Relation between Composition and Quality, Clin. Chem. 30(10): 1625–1630, Oct. 1984.*
Ford, A.W. et al. *J. Pharm. Pharmacol.* 45:900–906 (1993).*
"Clinical Chemistry", vol. 23, No. 6, pp. 1118–1119, 1977.

"Koso Handobukku (Enzyme Handbook)", Asakura Shoten (Publisher), Japan, pp. 434–435, 1983 and partial English language translation.

"Rinsho Kagaku (Clinical Chemistry)", vol. 19, No. 2, pp. 232–246, 1990 and partial English language translation.

"Seibutsu–Siryo–Bunseki (Journal of Analytical Bio– Science)", vol. 14, No. 2, pp. 81–89, 1991 and partial English language translation.

"Rinsyo–Kensa–Kiki–Shiyaku (The Journal of Clinical Laboratory, Instruments and Reagents)", vol. 15, No. 4, pp. 615–623, 1992 and partial English language translation.

"Kensa–to–Gijutsu (Modern Medical Laboratory)", vol. 20, No. 12, pp. 1039–1041, 1992 and partial English language translation.

"Kensa–to–Gijutsu (Modern Medical Laboratory)", vol. 21, No. 5, pp. 125–127, extra issue, 1993 and partial English language translation.

"Kensa–to–Gijutsu (Modern Medical Laboratory)", vol. 22, No. 8, p. 594, 1994 and partial English language translation.

* cited by examiner

Primary Examiner—Rebecca E. Prouty
Assistant Examiner—Richard Hutson
(74) Attorney, Agent, or Firm—Pennie & Edmonds LLP

(57) ABSTRACT

Disclosed is a stabilized enzyme composition for use in clinical examination, comprising: (a) an enzyme component comprising at least two enzymes selected from the group consisting of alkaline phosphatase, creatine kinase and alanine aminotransferase; (b) a stabilizer component comprising effective stabilizing amounts of an albumin, and at least one saccharide selected from the group consisting of trehalose and sorbitol; and (c) an aqueous medium having dissolved therein the components (a) and (b). The enzyme composition of the present invention is stable for a prolonged period of time not only under non-freeze refrigeration conditions, but also under freezing conditions or under conditions for non-freeze refrigeration after thawing of the frozen composition, as compared to the conventional enzymatic compositions. The enzyme composition of the present invention can be advantageously used for the purpose of checking the precision in measurement, correcting measured values and calibrating the amount and activity of an enzyme, in a clinical examination for measuring the enzymatic activity in a sample, such as serum or the like.

6 Claims, No Drawings

ENZYME COMPOSITION FOR USE AS A CLINICAL DIAGNOSTIC REAGENT

FIELD OF THE INVENTION

The present invention relates to a novel enzyme composition for use in clinical examination. More particularly, the present invention is concerned with a stabilized enzyme composition for use in clinical examination, comprising (a) an enzyme component comprising at least two enzymes selected from the group consisting of alkaline phosphatase, creatine kinase and alanine aminotransferase; (b) a stabilizer component comprising effective stabilizing amounts of an albumin, and at least one saccharide selected from the group consisting of trehalose and sorbitol; and (c) an aqueous medium having dissolved therein the components (a) and (b).

The enzyme composition of the present invention is stable for a prolonged period of time not only under non-freeze refrigeration conditions, but also under freezing conditions or under conditions for non-freeze refrigeration after thawing of the frozen composition, as compared to conventional enzyme compositions. Specifically, with respect to each of at least two enzymes contained in the enzyme composition of the present invention, the activity can be maintained, for a prolonged period of time, in the liquid state or in the frozen state (i.e., in a non-lyophilized state). Therefore, the enzyme composition of the present invention is advantageous from the economical viewpoint and from the viewpoint of ease in handling.

In a clinical examination for measuring the enzymatic activity in a sample, such as serum or the like, the enzyme composition of the present invention can be advantageously used for the purpose of checking the precision in measurement, correcting measured values and calibrating the activity of an enzyme in the sample.

PRIOR ART

In clinical examinations, for measuring the enzymatic activity in a sample, such as serum or the like, enzyme compositions are used for the purpose of checking the precision in measurement, correcting. measured values and calibrating the amount and activity of an enzyme in the sample. At present, as such enzyme compositions, various compositions containing a single type of enzyme or containing an enzyme system comprising a plurality of types of enzymes which participate in consecutive reactions are commercially available. These enzyme compositions are used as control serum for checking the precision in measurement and as reference materials (standard materials) for rectifying differences between measured values obtained in different testing facilities, and also as calibrators for calibrating the amount and activity of enzymes. [With respect to the terms "control serum", "reference material" and "calibrator", which will be further explained below, reference can be made, for example, to "Kensa-to-Gijutsu (MODERN MEDICAL LABORATORY)", vol. 22, No. 8, p. 594, 1994]. Such an enzyme composition is prepared by adding the same enzyme as the enzyme to be determined to a serum product, such as pooled human serum, pooled animal serum, human albumin, bovine serum albumin or the like.

As the enzyme to be added to a serum product in order to prepare an enzyme composition, various enzymes derived from human sources and animal sources have been reported. For example, as control sera, "Monitrol" and "Monitrol L" (registered trade marks; both manufactured and sold by International Reagents Corporation, Japan), each of which is produced by adding an enzyme from animal sources to pooled human serum, are commercially available as a lyophilized product and as a frozen product, respectively. As examples of commercially available reference materials, there can be mentioned "SERACLEAR-HE" (trade name; manufactured and sold by NIPPON SHOJI KAISHA, Ltd., Japan) which is produced by adding an enzyme from established human cell lines or human source (erythrocyte) to pooled human serum, and "Enzyme reference" which is produced by adding the above-mentioned human-derived enzyme to bovine serum albumin. Among these commercially available enzyme compositions, with respect to those containing pooled human serum as a serum product, there is a danger that they have been contaminated with a known virus (such as HIV) or an unknown virus. Therefore, in use of such enzyme compositions containing pooled human serum, minute care is required for preventing biohazard.

The enzymatic activity of each of these enzyme compositions is determined by using an enzymatic assay reagent specific for the enzyme in the enzyme composition. Generally, in the measurement of a catalytic activity, such as an enzymatic activity, the measured value greatly varies depending on not only the type and concentration of the substrate, but also the reaction conditions, such as pH and reaction temperature.

In judging the condition of a patient by utilizing the enzymatic activity in a sample from the patient, such as serum or the like, wherein the enzymatic activity is measured by a diagnostic reagent, the above-mentioned fact that the measured value of enzymatic activity varies depending on the measuring conditions poses a serious problem. Further, various kits of reagents for measurement of an enzymatic activity are sold by many manufacturers. When a plurality of samples from the same lot are individually measured by using a plurality of reagent kits wherein the measuring conditions are greatly different among the measurements, largely different measured values are obtained with respect to the samples from the same lot, thus causing a confusion in the diagnosis.

In order to solve the above-mentioned problem, socalled "recommended methods", each of which prescribes detailed measuring conditions agreed to by many scientists, have been proposed by scientific societies. For example, there can be mentioned a recommended method proposed by the International Federation of Clinical Chemistry (IFCC) and a recommended method proposed by the Japan Society of Clinical Chemistry (JSCC). However, such recommended methods have a problem in that they do not use an automatic analyzer and, therefore, cannot be used in a testing facility which has to deal with a large number of samples in a day. Accordingly, for enabling the accuracy of such a recommended method to be directly reflected in the test results obtained by using an automatic analyzer, it becomes necessary to use a reference material which has been measured with respect to the enzymatic activity thereof by using the recommended method. Specifically, a measured value obtained routinely by means of an automatic analyzer using commercially available reagents can be corrected based on a standard value obtained by the measurement of a reference material using a recommended method, so that the enzymatic activity of a sample can be accurately measured to obtain a reliable value which does not depend on the measuring conditions. Thus, by using a reference material, differences among measured values obtained by different testing facilities can be suppressed to a minimum.

As explained above, a reference material is used for reflecting the accuracy of a recommended method in a routine measuring method. Therefore, it is required that a reference material have the same properties as those of a human-derived sample. Recently, from the viewpoint of achieving the interchangeability of test data, the importance of reference materials have been greatly recognized, and a reference material produced using a human-derived enzyme has also been commercially available. There exist a wide variety of human-derived enzymes. Some human-derived enzymes assume the form of isozymes, for example, derived from different organs, which isozymes are identical to one another in the enzymatic function but are different from one another in characteristics, such as specificity to organs. Further, the content of an enzyme in human-derived serum varies depending on the individual as a source of the serum and on the disease condition of the individual as a source of serum. For example, it is well known that there are various types of alkaline phosphatases which are derived from placenta, small intestine and a tumor cell, and these various types of alkaline phosphatases exhibit largely different levels of activity depending on the type of the buffer solution which is used for adding the enzyme thereto.

On the other hand, control serum is generally used for checking the precision of the measurement of the enzymatic activity in a sample. Specifically, control serum is used for checking (based on the measured values obtained by the measurement using the control serum) whether or not reagents and equipment perform normal functions. Accordingly, with respect to control serum, rather than the level of the enzymatic activity, it is important that the enzymatic activity of the control serum does not change for the period of time during which the measurement by using the control serum is conducted.

On the other hand, a calibrator is used for determining a calibration factor for an enzyme to be tested. The calibrator is also used for checking the precision of the measurement of the enzymatic activity by a specific reagent for enzymatic activity. This means that the calibrator may function as control serum. Further, a material which is used for the calibration of the enzymatic activity of an enzyme may also be a reference material for the enzyme. Thus, in respect of the function and role in the measurement of enzymatic activity, it is considered that a calibrator is positioned between control serum and a reference material.

These enzyme compositions are usually sold in the form of a lyophilized product, a liquid product or a frozen product.

A lyophilized product has excellent storage stability, but has problems in that a denaturation of lipoprotein occurs during the lyophilization, so that a solution obtained by dissolving the lyophilized product in water or the like is likely to become turbid, and an error in measuring the volume is likely to occur. Further, it has frequently been observed that the activity of an enzyme contained in a lyophilized product changes at the dissolution of the lyophilized product. For example, it has been reported that, with respect to a lyophilized product, large differences in activity are observed between vials of a single lot [see "Kensa-to-Gijutsu (MODERN MEDICAL LABORATORY)", vol. 20, No. 12, p. 1041, 1992]. More illustratively, especially in the case of alkaline phosphatase, a serious problem is likely to occur. For example, it has been pointed out that alkaline phosphatase is reversibly deactivated by serum lipoprotein. Further, it has been observed that, when a commercially available lyophilized control serum is stored at 25° C. after being dissolved in water or the like, the alkaline phosphatase present in the serum exhibits a considerable increase in activity within 24 hours from the dissolution [see "Seibutsu-Siryo-Bunseki (Journal of Analytical Bio-Science)", vol. 14, No.2, 1991]. Thus, with respect to alkaline phosphatase, there has been no lyophilized product which is satisfactory in respect of the suppression of a change in the alkaline phosphatase activity after dissolution. Further, it has also been reported that the temperature of a liquid (usually, water) used for dissolution affects the activity of an enzyme. For example, with respect to a lyophilized enzyme composition containing creatine kinase, it has been reported that a solution obtained by dissolving it in a dissolution liquid at 2 to 8° C. exhibits a creatine kinase activity higher than that of a solution obtained by dissolving it in a dissolution liquid at room temperature [see "Rinsyo-Kensa-Kiki-Shiyaku (The Journal of Clinical Laboratory, Instruments and Reagents)" vol. 15, No. 4, 1992]. From these reports, it can be concluded that the period during which a solution obtained by dissolving a lyophilized enzyme composition in a dissolution liquid is stable is as short as one or two days.

By contrast, with respect to a product in liquid or frozen state, it is not necessary to dissolve the product in a dissolution liquid (usually, water), so that the operation before usage is relatively easy, and an error in a dissolution operation does not occur. Further, the problem of the change in enzymatic activity at dissolution, which is disadvantageously large in the case of a lyophilized product, is eliminated. In using a frozen product, a thawing operation is necessary, whereas a product in liquid state can be used as it is, so that the use of products in liquid state has recently been increased also in the field of clinical biochemical examinations. A product in liquid state is also called a "reagent usable without reconstitution", since it can be used without a preparatory operation, such as thawing, dissolution or the like. Reagents usable without reconstitution enable simplification of operations and saving of man power in biochemical examination facilities.

Therefore, in the future, enzyme compositions for use in clinical examinations, such as control serum, a reference material, a calibrator and the like, would necessarily be provided as reagents usable without reconstitution. However, with respect to the above-mentioned enzyme compositions for use in clinical examinations, at the current technological level, it is impossible to provide them in the form of reagents usable without reconstitution. The only form of an enzyme composition which is practically usable at present is the frozen form. Moreover, with respect to a frozen product containing alkaline phosphatase, it is reported that a gradual increase in enzymatic activity is observed after thawing [see "Kensa-to-Gijutsu (MODERN MEDICAL LABORATORY)", vol. 20, No. 12, p. 1039, 1992]. Also, with respect to an enzyme composition containing creatine kinase frozen at −20° C., it has been reported that a decrease in the activity of creatine kinase is observed when the freeze storage period exceeds 1 to 3 months [see "Kensa-to-Gijutsu (MODERN MEDICAL LABORATORY)", vol. 21, No. 5, extra issue, 1993]. Thus, frozen products available at present are not always satisfactory.

In clinical examinations, alkaline phosphatase is useful not only as a tumor marker, but also as means for obtaining much information on the condition of disease. Creatine kinase has 3 isozymes and is extremely localized in specific organs, as compared to enzymes, such as alanine aminotransferase, aspartate aminotransferase and the like, which are widely used in clinical examinations at present. Most creatine kinase is present in skeletal muscles, cardiac muscle, smooth muscle and the brain. Accordingly, by determining creatine kinase, identification of injury of creatine kinase-related organs would be able to be made. Therefore, it is desired to develop a stabilized enzyme composition containing at least alkaline phosphatase and creatine kinase, especially in a liquid form or a frozen form, which can be used as control serum, a reference material or a calibrator.

In general, an enzyme is a protein and, therefore, a solution of an enzyme is unstable. As a method for obtaining an enzyme having improved stability, a method is known in which a thermophilic microorganism is cultured and then, an enzyme is obtained from the resultant culture of the thermophilic microorganism. This method is effective because thermophilic microorganisms produce thermostable enzymes. In recent years, it has become possible to design or modify a thermostable enzyme, using the techniques of protein engineering, based on the information on the genes, amino acids, steric structures and the like of proteins. On the other hand, for improving the stability of an enzyme, various methods have been proposed in which the composition of a solution containing the enzyme is adjusted or modified.

For example, a polyol, such as glycerol, is known as a generally employed stabilizing agent. However, a vast plurality of types of enzymes are known, and their properties, such as optimum pH and the like, are also diversified. A stabilizing agent which is effective for all of the enzymes has not been reported. On the other hand, various reports have been made on the method for stabilizing a single specific enzyme.

For example, a creatine kinase composition having improved stability, which is obtained by using as a stabilizing agent a protein having an unreactive sulfhydryl group, is disclosed in Unexamined Japanese Patent Application Laid-Open Specification No. 5-207880 (corresponding to U.S. Pat. No. 5,217,890). Further, U.S. Pat. No. 5,298,406 discloses a creatine kinase composition having improved stability which comprises ascorbic acid and non-reducing polyol as stabilizers (antioxidants) and an aminoglycoside antibiotic as an antimicrobial agent. All of the above-mentioned stabilizers are intended to stabilize the SH group which is essential for the activity of creatine kinase.

It has long been believed that, when a composition contains two or more enzymes, such as creatine kinase and alkaline phosphatase, it is difficult to find out conditions effective for stabilizing all of the enzymes in the composition, since the conditions effective for stabilizing an enzyme frequently render another enzyme unstable. For example, a magnesium ion is not only necessary for activating alkaline phosphatase [see "Koso Handobukku (Enzyme Handbook)", p 434, published in 1983 by Asakura Shoten, Japan], but also functions as a stabilizer for alkaline phosphatase. However, on the other hand, it is well known that the storage stability of creatine kinase is increased by the addition of a chelating reagent, which coordinates to a metal ion, such as magnesium ion, to form a chelate with the metal ion (see Clin. Chem., 23, 1119, 1977). Thus, a stabilizing agent for alkaline phosphatase and that for creatine kinase are opposite or incompatible to each other in properties. Further, since creatine kinase is an SH enzyme as described above, it is stabilized in the presence of a thiol compound, such as cysteine, mercaptoethanol, N-acetylcysteine, cysteinyl-bovine serum albumin described in the above-mentioned Unexamined Japanese Patent Application Laid-Open Specification. On the other hand, the presence of cysteinyl-bovine serum albumin renders alkaline phosphatase unstable, and, as shown in Example 1 below, N-acetylcysteine also renders alkaline phosphatase unstable.

Still further, it has been reported that the conditions effective for the stabilization of an enzyme composition in a liquid form is generally different from those effective for the stabilization of the enzyme composition in a frozen form, and therefore it is difficult to find out conditions under which an enzyme composition is stabilized either in a liquid form or in a frozen form. For example, the freeze storage stability of alkaline phosphatase is lowered by the addition of sucrose (see Example 5 of the present application). It has also been reported that the stability of lactate dehydrogenase is rather decreased at a low temperature [see Rinsho Kagaku (Clinical Chemistry) vol. 19, No. 2, 1990], despite the fact that an enzyme is generally known to be more stable at a lower temperature.

In some cases of clinical examination, the activity of an enzyme (first enzyme) is measured utilizing another enzyme (second enzyme) which participates in the enzyme reaction together with the first enzyme. In recent years, a reagent kit for measurement of enzymatic activity, in which the above-mentioned second enzyme is contained in a stabilized form, has been developed as a kit of reagents usable without reconstitution. In the case of such an enzyme composition, the stability of the enzymatic activity is not very important as long as the enzymatic activity is maintained to some extent. Therefore, the enzyme may be contained in an excess amount in order to make up for a lowering of the enzymatic activity. However, with respect to an enzyme composition for use in a clinical examination for the purpose of checking the precision in measurement, correcting measured values and calibrating the amount or enzymatic activity of an enzyme, such as a reference material, a calibrator or control serum, the stability of the enzymatic activity is a very important factor influencing the commercial value of the enzyme composition. The stabilization of an enzyme composition for use in checking the precision in measurement, correcting measured values and calibrating the amount or enzymatic activity of an enzyme is very difficult not only for the reasons described above but also because the concentration of the enzyme is very small.

In these situations, it has been desired to develop a stabilized enzyme composition containing at least two enzymes (at least two enzymes selected from the group consisting of alkaline phosphatase, creatine kinase and alanine aminotransferase), wherein each of the enzymes exhibits almost no lowering of activity during storage, which enzyme composition can be advantageously used for checking the precision in measurement, correcting measured values and calibrating the amount or enzymatic activity of an enzyme.

SUMMARY OF THE INVENTION

In these situations, the present inventors have made extensive and intensive studies with a view toward developing a stabilized enzyme composition which contains at least two enzymes selected from the group consisting of alkaline phosphatase, creatine kinase and alanine aminotransferase which are important in clinical examination, which composition can be advantageously used in clinical examination for checking of the precision in measurement, correction of a measured value, and/or calibration. As a result, it has unexpectedly been found that, when a combination of a specific saccharide and an albumin is used as a stabilizer for an enzyme composition, all of the enzymes contained in the enzyme composition can maintain their respective activities for a prolonged period, not only in a liquid form without experiencing freezing, but also in a frozen form and in a liquid form after thawing of the once frozen product, as compared to a conventional enzyme composition containing only one enzyme which is commercially available and is used for the same purpose as mentioned above. The present invention has been completed, based on the above finding.

Therefore, it is a primary object of the present invention to provide an enzyme composition for use in clinical examination, containing at least two enzymes selected from the group consisting of alkaline phosphatase, creatine kinase and alanine aminotransferase, wherein the activities of all of the enzymes contained in the enzyme composition are stabilized, so that the composition is not only advantageous from an economical viewpoint, but also useful as control serum, a reference material or a calibrator which enables extremely reliable measurement with very small variation in measured values, as compared to the conventional enzyme compositions containing only one enzyme.

DETAILED DESCRIPTION OF THE INVENTION

Essentially, in the present invention, there is provided a stabilized enzyme composition for use in clinical examination, comprising:

(a) an enzyme component comprising at least two enzymes selected from the group consisting of alkaline phosphatase, creatine kinase and alanine aminotransferase;

(b) a stabilizer component comprising effective stabilizing amounts of an albumin, and at least one saccharide selected from the group consisting of trehalose and sorbitol; and (c) an aqueous medium having dissolved therein the components (a) and (b).

By virtue of the presence of a stabilizer component comprising an albumin, and at least one saccharide selected from the group consisting of trehalose and sorbitol, the enzyme composition of the present invention exhibits excellent stability, with respect to the activities of all of the enzymes contained in the composition, not only under freezing conditions but also under non-freeze refrigeration conditions, irrespective of whether or not the composition has an experience of being frozen.

In an essential aspect of the present invention, the enzyme component of the enzyme composition comprises a plurality of enzymes, namely, at least two enzymes selected from the group consisting of alkaline phosphatase (ALP) (EC.3.1.3.1), creatine kinase (CK) (EC.2.7.3.2) and alanine aminotransferase (ALT) (EC.2.6.1.2), differing from the conventional enzyme composition containing a single enzyme. Representative examples of combinations of at least two enzymes include a combination of two enzymes ALP and CK, and a combination three enzymes ALP, CK and ALT.

Further, in the present invention, it is preferred that the enzyme component of the enzyme composition further comprises at least one additional enzyme selected from the group consisting of aspartate aminotransferase (AST) (EC.2.6.1.1), lactate dehydrogenase (LDH) (EC.1.1.1.27) and γ-glutamyl transpeptidase (γ-GTP) (EC.2.3.2.2). Representative examples of at least one additional enzyme include AST singly used, and a combination of three enzymes AST, LDH and γ-GTP.

It is most preferred that the enzyme component of the enzyme composition of the present invention comprises ALP, CK and ALT, as enzyme component (a), and AST, LDH and γ-GTP as additional enzymes.

When the composition of the present invention comprises the components described in the above-mentioned essential aspect of the present invention, it is preferred that, when selected as a constituent of the enzyme component (a), the alkaline phosphatase is present in a concentration of from 9 to 6500 U, the creatine kinase is present in a concentration of from 6 to 4000 U, and the alanine aminotransferase is present in a concentration of from 3 to 1150 U, each per liter of the composition.

With respect to the effective stabilizing amount of the stabilizer component (b), it is preferred that the albumin is present in a concentration of from 0.3 to 7 (w/v) %, and the at least one saccharide selected from the group consisting of trehalose and sorbitol is present in a concentration of from 2 to 15 (w/v) %, each based on the volume of the composition.

Examples of albumins used as a part of the stabilizer component include an albumin obtained from a mammal, such as human serum albumin and bovine serum albumin (BSA), and an albumin obtained from a bird, such as chick serum albumin. As these albumins, commercially available albumins can be used. It is preferred that the concentration of the albumin in the enzyme composition of the present invention is from 0.3 to 7 (w/v) %, more preferably from 1 to 5 (w/v) %.

At least one saccharide used as a part of the stabilizer component is selected from the group consisting of trehalose and sorbitol. It is preferred that the concentration of the at least one saccharide in the enzyme composition of the present invention is from 2 to 15 (w/v) %, more preferably from 3 to 10 (w/v) %. For controlling the viscosity of the composition with ease and for achieving a satisfactory stabilizing effect, the concentration of the at least one saccharide is preferred to fall within the range mentioned above. If desired, the at least one saccharide can be a mixture of sorbitol and trehalose.

When the enzyme component (a) further comprises the at least one additional enzyme selected from the group consisting of aspartate aminotransferase, lactate dehydrogenase and γ-glutamyl transpeptidase, it is preferred that, when selected as the additional enzyme, the aspartate aminotransferase is present in a concentration of from 3 to 1150 U, the lactate dehydrogenase is present in a concentration of from 8 to 4000 U, and the γ-glutamyl transpeptidase is present in a concentration of from 2 to 1200 U, each per liter of the composition. If desired, amylase, lipase or the like can be added to the composition. It is preferred that, when added to the composition, amylase is present in a concentration of from 25 to 1000 U, and lipase is present in a concentration of from 5 to 1000 U, each per liter of the composition.

With respect to the activity of an enzyme, the amount of the enzyme required to convert 1 μmol of the substrate at 37° C. is defined as 1 U. For example, with respect to each of ALP, CK, ALT, AST and LDH, the activity thereof can be determined by the consensus method which is the same method as the recommended method proposed by the Japanese Society of Clinical Chemistry ["Rinsho Kagaku (Japanese Journal of Clinical Chemistry)", vol. 19, p.184 and p.209 (1990); ivid, vol. 18, p.211 and p.226 (1989); ivid, vol. 19, p.228 (1990)], except that the measurement temperature is changed from 30° C. to 37° C., or can be determined by using commercially available reagents (such as reagents used in the Examples mentioned below) for the determination of the enzymatic activity of a respective enzyme. The activity of γ-GTP can be determined by using a commercially available kit for the determination of the activity of the enzyme ('Determiner γ-GTP', manufactured and sold by KYOWA MEDEX Co., Ltd., Japan), which kit uses γ-glutamyl-3,5-dibromo-4-hydroxyanilide as a substrate. This substrate is converted by the action of γ-GTP to 3,5-dibromo-4-hydroxyanilide (DBHA), and the generated DBHA is oxidatively condensed with 1-N-ethyl-N-(3-methylphenol)-N-succinyl ethylenediamine (EMSE) by the action of a monophenol monooxygenase (MPO), such as ascorbate oxydase, laccase or the like, to thereby generate a green condensate exhibiting an absorption at a wavelength of 710 nm. The activity of γ-GTP can be determined by calorimetric determination of the condensate.

With respect to the origin of the enzymes used for producing the enzyme composition of the present invention, there is no particular limitation as long as the enzymes are suitable as a component for an enzyme composition which is provided in a liquid form or frozen form. However, it is preferred that each of the enzymes is derived from an animal, more preferably from human.

With respect to the enzymes derived from an animal, examples of alkaline phosphatase (ALP) include bovine kidney ALP (catalog No. P6680, Sigma Chemical Company, U.S.A.), bovine intestinal ALP (catalog No. P0280, Sigma Chemical Company, U.S.A.), hog kidney ALP (catalog No. P4439, Sigma Chemical Company, U.S.A.), chick intestinal ALP (catalog No. P8008, Sigma Chemical Company, U.S.A.) and the like. Examples of creatine kinase (CK) include bovine heart CK (catalog No. C7886, Sigma Chemical Company, U.S.A.), hog heart CK [tradename: 'Monitrol (L)', International Reagents Corporation, Japan], chick heart CK (tradename: 'Control WAKO', Wako Pure Chemical Industries Ltd., Japan), rabbit muscle CK (catalog No. C3755, Sigma Chemical Company, U.S.A.) and the like. Examples of aspartate aminotransferase (AST) include bovine heart AST (tradename: 'Monitrol II', International Reagents Corporation, Japan), hog heart AST (catalog No. G2751, Sigma Chemical Company, U.S.A.) and the like. Examples of alanine aminotransferase (ALT) include bovine heart ALT (tradename: 'Monitrol II', International Reagents Corporation, Japan), hog heart ALT (catalog No. G8225, Sigma Chemical Company, U.S.A.) and the like. Examples of lactate dehydrogenase (LDH) include chick heart LDH (catalog No. L9126, Sigma Chemical Company, U.S.A.), hog heart LDH (catalog No. L2881, Sigma Chemical Company, U.S.A.) and the like. Examples of γ-glutamyl transpeptidase (γ-GTP) include bovine kidney γ-GTP (catalog No. G4135, Sigma Chemical Company, U.S.A.), hog kidney γ-GTP (catalog No. G2262, Sigma Chemical Company, U.S.A.) and the like.

An enzyme used in the present invention can be obtained from a biological material, derived from a human body, containing the enzyme, such as serum, erythrocytes, urine or the like; from a culture of cells, derived from human, capable of producing the enzyme; or from a culture of transformed cells, to which a human gene coding for the enzyme has been integrated by gene recombination technique, capable of producing the enzyme. Examples of enzymes obtained from a biological material derived from a human body include AST and LDH each obtained from erythrocyte, and γ-GTP obtained from urine. Each of these enzymes can be obtained from the above-mentioned biological material by conventional methods. Preferred examples of cells derived from human include human hepatitis cancer cell strain BRL68 (deposited at ATCC under the accession number CL-48), human Burkitt's lymphoma cell strain Namalwa cell (deposited at ATCC under the accession number CRL-1432), human promyeloid leukemia cell strain HL-60 (deposited at ATCC under the accession number CCL-240) and the like. The above-mentioned enzymes can be obtained from cultures of these cells by conventional methods.

With respect to each of the enzymes used in the present invention, there have been a number of reports about cDNA coding for the enzyme obtained from animals or human. Therefore, it is possible to obtain the enzyme from a culture of transformed cells, to which the gene coding for the enzyme has been integrated. With respect to the cells used to obtain the culture of transformed cells, use can be made of not only the cells derived from human, but also the cells derived from an animal other than human, such as CHO cells derived from a Chinese hamster. Further, even cells of microorganisms, such as *Escherichia coli*, can be used to obtain the culture of transformed cells. In the present invention, if desired, each of the above-mentioned enzymes (including the enzymes obtained using the cells of an animal and the enzymes obtained from a biological material derived from a human body, or from a culture of cells derived from human) can be purified by using various conventional methods (such as column chromatography) in combination, before the enzyme is used to prepare the composition of the present invention.

In the present invention, when the enzyme composition contains alkaline phosphatase, an ionic magnesium (preferably, magnesium chloride) is generally added to the composition in an amount such that the composition has a magnesium concentration of from 0.05 to 30 mM, preferably from 0.1 to 5 mM for stabilizing the composition.

With respect to the aqueous medium used as component (c) of the present invention, there is no particular limitation, as long as the aqueous medium has a buffer capacity to maintain the pH of the enzyme composition at a level around neutral pH, preferably around 7 to 8. For example, as component (c), a Good's buffer solution (which can be prepared, for example, by dissolving a buffer, such as PIPES, HEPES or BES, in distilled water, followed by adjusting the pH of the resulting solution by NaOH), a phosphate buffer solution or the like can be used in a concentration of from 5 to 200 mM, preferably from 10 to 100 mM. If desired, an antiseptic agent or the like can be added to the aqueous medium.

As mentioned above, the enzyme composition of the present invention exhibits excellent storage stability, not only when the composition is stored in a frozen form, but also when the composition is stored in a liquid form under non-freeze refrigeration conditions irrespective of whether or not the composition has an experience of being frozen. That is, the advantageous effect of the composition of the present invention can be achieved irrespective of whether the composition is in a liquid form or a frozen form.

Since the enzymatic activity of the enzyme composition of the present invention is to be compared with the enzymatic activity of a biological sample, such as serum, plasma or the like, it is preferred that the physicochemical properties of the enzyme composition of the present invention, such as viscosity, specific gravity or the like, are similar to those of the biological sample to be tested. In general, when there is a difference in physicochemical properties between a biological sample (in many cases serum) and an enzyme composition, an error frequently occurs in effecting sampling by an automatic analyzer, so that accurate determination of the enzymatic activity cannot be performed ["Kensa to Gijutu (Examination and Technology)", Vol.17, No.2, 1989]. Further, it should be noted that when a stabilizer is added to an enzyme composition, the physicochemical properties of the enzyme composition actually, frequently become much different from those of serum than those of the enzyme composition before the addition of the stabilizer.

By contrast, the physicochemical properties of the enzyme composition of the present invention, such as viscosity, specific gravity or the like, can be easily caused to approximate to those of a biological sample to be tested, e.g. serum. The viscosity and specific gravity of human serum have been reported to be in the range of from 1.07 to 1.39 cP (as measured at 37° C.) and in the range of from 1.0180 to 1.0244 (as measured at 25° C.), respectively, although they are different among individuals [see the Research Reports by HEM (human-derived enzyme materials) working groups, p.21, June, 1992]. As mentioned above, the composition of the present invention can be provided in a liquid form or a frozen form. It is preferred that the composition of the present invention has a specific gravity of from 1.015 to 1.030 at 25° C., and a viscosity of from 1.05 to 1.40 cP at 37° C. respectively, each as directly measured when the composition is in a liquid form, or as measured after thawing the composition when the composition is in a frozen form. For example, when sorbitol as a saccharide and BSA as an albumin are used in the composition of the present invention, wherein the content of BSA is 3% and the content of sorbitol is 3%, the composition has a viscosity of 1.18 cP and a specific gravity of 1.01839. When the content of BSA is 3% and the content of sorbitol is 5%, the composition has a viscosity of 1.30 cP and a specific gravity of 1.02508. These viscosity and specific gravity values fall almost within the above-mentioned ranges of the viscosity and specific gravity of human serum. The viscosity is measured under the conditions of 37° C., 50 rpm and 48 cones by means of Biorheolizer (manufactured and sold by Toki Sangyo Co., Ltd., Japan). The specific gravity is measured at 25° C. by means of Gay-Lusac pycnometer.

The enzyme composition of the present invention can be prepared, for example, at a low temperature, preferably at 2 to 8° C., by the following method. That is, the enzyme composition of the present invention can be prepared by weighing each of the components (a) to (c), dissolving each of the components (a) and (b) in component (c) (an aqueous medium) in predetermined concentrations, and adjusting the pH of the resultant solution. Further, the obtained composition may be dispensed in glass containers, such as vials, in an amount of from 1 to 10 ml per container. The dispensed composition may be used as such, or frozen at −20° C. or less by means of a freezing machine as soon as possible after the preparation thereof, and stored in the frozen state. The enzyme composition in the frozen state is used after it has been thawed spontaneously at room temperature, preferably at 2 to 25° C., and homogenized.

When the enzyme composition of the present invention is used as control serum, a reference material or a calibrator in clinical examination for the determination of an enzymatic activity, the activity of each of the enzymes contained in the composition can be determined by the same method as that for determining an enzymatic activity in a biological sample, such as serum, using reagents appropriate for determination of the enzymatic activity. Specifically, when the enzyme composition is in a liquid form, it can be used as such; and when the composition is in a frozen form, it can be used after thawing of the frozen composition. A portion of the composition dispensed in a vial is sampled into a sample cup of an automatic analyzer in an amount of, for example, 0.1 to 0.5 ml, and then the sample cup is set in the automatic analyzer. The composition of the present invention can be stored under non-freeze refrigeration conditions at, for example, 2 to 8° C. for at least 1 week after preparation.

During this storage period, the activity of any of the enzymes contained in the composition is stable and undergoes no lowering. When the composition is not used immediately after preparation, the composition can be stored in the frozen state at −20° C. or less and used after being thawed. In this case, the activity of any of the enzymes contained in the composition stored in the frozen state at −20° C. or less is stable and undergoes no lowering for at least 15 months. Further, when the frozen composition is thawed and stored at 2 to 8° C., the activity of each of the enzymes can be maintained for 1 week, as in the case of the composition immediately after preparation.

That is, the enzyme composition of the present invention is a stabilized enzyme composition suitable for use in clinical examination, which can be stably stored and suffers almost no lowering of the activity of any of the enzymes contained in the composition for a relatively long period of time, namely, for at least 1 week after preparation under non-freeze refrigeration conditions at 2 to 8° C.; for at least 15 months under freezing conditions (in which the composition is in the frozen state) at −20° C. or less; and for at least 7 days under conditions for non-freeze refrigeration at 2 to 8° C. after thawing of the frozen composition. The enzyme composition of the present invention is generally used in an amount of from about 5 to about 500 μl in every measurement operation in clinical examination.

BEST MODE FOR CARRYING OUT THE INVENTION

The present invention will be further illustrated in more detail with reference to the following Reference Examples and Examples, which should not be construed as limiting the scope of the present invention.

The measurement of the enzymatic activity in Reference Examples and Examples was conducted at 37° C. using the following commercially available reagents. When the activity of γ-glutamyl transpeptidase (γ-GTP) was measured, the calibrator attached to the reagents was used for determining the enzymatic activity. With respect to the enzymes other than γ-GTP, the enzymatic activity was determined by a method using the calibration factor (K factor) which is obtained by the measurement using an indicator compound [see "Kensa-to-Gijutsu" (MODERN MEDICAL LABORATORY)", vol.25, No.5, p223, Extra issue in 1993]. An auto-analyzer (7070 type manufactured and sold by Hitachi, Ltd., Japan) was used for the measurement of the enzymatic activity.

| Enzyme | Reagents for measurement |
| --- | --- |
| asparatate aminotranferase (AST) | GOTII-HA test-WAKO (manufactured and sold by WAKO PURE CHEMICAL Industries Ltd., Japan) |
| alanine aminotranferase (ALT) | GPTII-HA test-WAKO (manufactured and sold by WAKO PURE CHEMICAL Industries Ltd., Japan) |
| λ-glutamyl transpeptidase (λ-GTP) | Determiner λ-GTP (manufactured and sold by KYOWA MEDEX Co., Ltd., Japan) |
| alkaline phosphatase (ALP) | ALPII-HA test-WAKO (manufactured and sold by WAKO PURE CHEMICAL Industries Ltd., Japan) |
| creatine kinase | CPKII-HA test-WAKO |

| Enzyme | Reagents for measurement |
| --- | --- |
| (CK) | (manufactured and sold by WAKO PURE CHEMICAL Industries Ltd., Japan) |
| lactate dehydrogenase (LDH) | LDHII-HA test-WAKO (manufactured and sold by WAKO PURE CHEMICAL Industries Ltd., Japan) |

REFERENCE EXAMPLE 1

Human promyeloid leukemia cell strain HL-60 (deposited at ATCC under the accession number CCL-240) was dispersed in a RPMI-1640 medium (manufactured and sold by Sigma Chemical Company, USA) containing fetal bovine serum added thereto in an amount of 10% (v/v), so that the resultant suspension had a cell density of $1\times10^5$ cells/ml. 1.5 Liters of the obtained cell suspension were charged into a 2 liter spinner flask and were subjected to suspension culture with agitation for 5 days in a carbon dioxide incubator which was set to have 37° C. and an atmosphere consisting of air (95%) and carbon dioxide (5%). The cultured cells were separated by means of a centrifuge and then, disrupted by ultrasonication. The enzymatic activity of the supernatant was measured with respect to the cell density of $10^7$ cells/ml. As a result, 6435 U/liter of LDH, 260 U/liter of AST and 5300 U/liter of CK-were detected. The supernatant of the mixture obtained by the disruption of the cultured cells was subjected to ammonium sulfate fractionation, and then to column chromatographic fractionation using DEAE-Sepharose CL-6B column (manufactured and sold by Pharmacia Fine Chemicals AB, Sweden), to thereby obtain a mixed fraction of AST and LDH and a CK fraction. The mixed fraction of AST and LDH was subjected again to column chromatographic fractionation using Blue-Sepharose CL-6B column (manufactured and sold by Pharmacia Fine Chemicals AB, Sweden), so that AST was obtained from the fraction passing through the column and LDH was obtained from the fraction adsorbed on the column.

REFERENCE EXAMPLE 2

Human fetal hepatic cell strain BRL68 (deposited at ATCC under the accession number CL-48) was dispersed in a commercial MEM medium containing fetal bovine serum added thereto in an amount of 10% (v/v), so that the resultant suspension had a cell density of $2.5\times10^4$ cells/ml. 200 ml of the obtained cell suspension was charged into each of 225 ml flasks for tissue culture [manufactured and soled by Sumitomo Bakelite Co., Ltd., Japan] and was subjected to static culture for 4 days in a carbon dioxide incubator which was set to have 37° C. and an atmosphere consisting of air (95%) and carbon dioxide (5%). 0.01% (w/v) trypsin solution (manufactured and soled by GIBCO, USA) was added to the cultured cells so as to remove the cultured cells from the inner surface of the flask. The cells were collected by means of a centrifuge and then, disrupted by ultrasonication. The enzymatic activity of the supernatant was measured with respect to the cell density of $10^7$ cells/ml, and 14650 U/liter of LDH, 811 U/liter of AST and 1473 U/ml of ALP were detected. The supernatant of the mixture obtained by the disruption of the cultured cells was subjected to ammonium sulfate fractionation, and then to column chromatographic fractionation using Blue-Sepharose CL6B column (manufactured and sold by Pharmacia Fine Chemicals AB, Sweden). ALP was obtained from the fraction passing through the column.

EXAMPLE 1

Enzyme compositions having the following composition were provided:

20 mM PIPES-NaOH (pH 7.5),

3% BSA (bovine serum albumin) (manufactured and sold by Sigma Chemical Company, USA), 500 U/liter ALP (hog kidney-derived; manufactured and sold by Sigma Chemical Company, USA), and 250 U/liter CK (rabbit muscle-derived; Boehringer-Mannheim GmbH, Germany).

From the enzyme compositions, the following samples were prepared:

(1) a sample having the above composition, which contains ALP and CK, (2) a sample which was prepared by adding 1 mM of N-acetylcysteine (manufactured and sold by Sigma Chemical Company, USA) to sample (1) above, (3) a sample which was prepared by adding 0.5 mM of magnesium chloride to sample (1) above, (4) a sample which was prepared by adding 5% sorbitol (manufactured and sold by WAKO PURE CHEMICAL Industries, Japan) to sample (1) above, and (5) a sample which was prepared by adding 0.5 mM of magnesium chloride and 3% sorbitol to sample (1) above.

The residual enzymatic activity after the storage at 37° C. for one day was measured with respect to each of samples (1) to (5). The respective residual activities (%) of ALP and CK are shown in Table 1 with respect to each sample.

TABLE 1

Residual activity (%) after storage at 37° C. for one day

| | Additives other than BSA | Enzyme | Residual activity (%) |
| --- | --- | --- | --- |
| Controls | (1) None | ALP CK | 65 90 |
| | (2) N-acetylcysteine | ALP CK | 34 98 |
| | (3) MgCl$_2$ | ALP CK | 75 63 |
| Present invention | (4) Sorbitol | ALP CK | 98 99 |
| | (5) Sorbitol MgCl$_2$ | ALP CK | 100 99 |

As shown in Table 1, with respect to sample (1) in which only BSA was added to a buffer solution of enzymes, the respective residual activities of ALP and CK were caused to lower as compared to the original activities. With respect to sample (2) in which N-acetylcysteine was added, the residual activity of ALP was caused to lower even as compared to that in sample (1), although the residual activity of CK was a little improved as compared to that in sample (1). With respect to sample (3) which had magnesium chloride added thereto, contrary to the case of sample (2), the residual activity of ALP was a little improved as compared to that in sample (1), whereas the residual activity of CK was caused to lower as compared to that in the sample (1). By contrast, with respect to samples (4) and (5), both of which are the stabilized enzyme compositions of the present invention, almost no lowering of the activity of each of ALP and CK was observed.

EXAMPLE 2

Enzyme compositions having the following composition were provided:

20 mM BES-NaOH (pH 7.5),
3% BSA (manufactured and sold by Sigma Chemical Company, USA),
0.5 mM magnesium chloride,
2 mM alanine,
526 U/liter ALP (hog kidney-derived; manufactured and sold by Sigma Chemical Company, USA),
303 U/liter CK (rabbit muscle-derived; Boehringer-Mannheim GmbH, Germany), and
108 U/liter ALT (hog heart-derived; manufactured and sold by Sigma Chemical Company, USA).

To the above-provided enzyme compositions were respectively added trehalose, sorbitol, mannitol, galactose and lactose, each in a concentration of 5%.

With respect to each of the resultant samples containing a saccharide, the storage stability in a liquid form was examined after the storage at 5° C. and the storage stability in a frozen form was examined after the storage at −20° C.

The respective residual activities (%) of the enzymes after the storage at 5° C. for 3 weeks are shown in Table 2. The respective residual activities (%) of the enzymes after the storage at −20° C. for 3 weeks are shown in Table 3.

TABLE 2

Residual activity (%) after storage at 5° C. for 3 weeks

|  | Saccharide | ALT | ALP | CK |
|---|---|---|---|---|
| Controls | None | 95 | 99 | 94 |
|  | Mannitol | 95 | 98 | 94 |
|  | Galactose | 90 | 103 | 95 |
|  | Lactose | 87 | 109 | 95 |
| Present invention | Trehalose | 98 | 99 | 100 |
|  | Sorbitol | 99 | 99 | 98 |

TABLE 3

Residual activity (%) after storage at −20° C. for 3 weeks

|  | Saccharide | ALT | ALP | CK |
|---|---|---|---|---|
| Controls | None | 97 | 96 | 95 |
|  | Mannitol | 82 | 94 | 92 |
|  | Galactose | 100 | 104 | 99 |
|  | Lactose | 100 | 103 | 101 |
| Present invention | Trehalose | 101 | 99 | 98 |
|  | Sorbitol | 100 | 98 | 98 |

As shown in Table 2, when the samples were stored at 5° C. for 3 weeks, with respect to the residual activity of each of the samples respectively having galactose and lactose added thereto, the activity of ALT was caused to lower by approximately 10% as compared to the original activity. With respect to the residual activity of each of the sample containing no saccharide and the sample having mannitol added thereto, the activity of ALT was caused to lower by approximately 5% as compared to the original activity. The activity of ALP was maintained at substantially the same level as the original level of activity, with respect to all of the samples (including the sample containing no saccharide). The activity of CK was caused to lower by approximately 5% with respect to the samples falling outside the scope of the present invention.

As shown in Table 3, when the samples were stored at −20° C. for 3 weeks, with respect to the residual activity of the sample containing no saccharide, the activity of CK was caused to lower by approximately 5% as compared to the original activity. With respect to the sample having mannitol added thereto, the activity of ALT was caused to lower by approximately 18%, the activity of ALP was caused to lower by approximately 6% and the activity of CK was caused to lower by approximately 8%, as compared to the respective original activities.

By contrast, with respect to the samples respectively having sorbitol and trehalose added thereto, both of which are the stabilized enzyme compositions of the present invention, almost no lowering of the activity of each of the enzymes contained therein was observed under both storage conditions of 5° C. and −20° C.

EXAMPLE 3

Enzyme compositions having the following composition were provided:

20 mM PIPES-NaOH (pH 7.5),
0.3% BSA (manufactured and sold by Sigma Chemical Company, USA),
0.5 mM magnesium chloride,
0.5 mM calcium chloride,
10 mM sodium glutamate
536 U/liter ALP (hog kidney-derived; manufactured and sold by Sigma Chemical Company, USA),
301 U/liter CK (rabbit muscle-derived; Boehringer-Mannheim GmbH, Germany),
100 U/liter AST (hog heart-derived; manufactured and sold by Sigma Chemical Company, USA), and
108 U/liter ALT (hog heart-derived; manufactured and sold by Sigma Chemical Company, USA).

From the above enzyme compositions were prepared three samples, namely, a sample having 5% sucrose added thereto, a sample having 5% trehalose added thereto, and a sample having no saccharide added thereto.

Each of the samples was stored at −20° C. in a frozen form. The respective residual activities (%) of the samples after the storage at −20° C. for 6 months are shown in Table 4.

TABLE 4

Residual activity (%) after storage at −20° C. for 6 months

|  | Saccharide | AST | ALP | CK | ALT |
|---|---|---|---|---|---|
| Controls | None | 101 | 92 | 100 | 99 |
|  | Sucrose | 99 | 85 | 99 | 97 |
| Present invention | Trehalose | 100 | 100 | 100 | 99 |

As shown in Table 4, when the samples were stored at −20° C. for 6 months, with respect to the sample having sucrose added thereto, the activity of ALP was caused to lower by approximately 15% as compared to the original activity. With respect to the sample containing no saccharide, the activity of ALP was caused to lower by approximately 10% as compared to the original activity. By contrast, with respect to the sample having trehalose added thereto, which is the stabilized enzyme composition of the present invention, almost no lowering of the activity of each of AST, ALT, ALP and CK was observed.

EXAMPLE 4

Enzyme compositions having the following composition were provided:

20 mM BES-NaOH (pH 7.5),

3% BSA (manufactured and sold by Sigma Chemical Company, USA), 2 mM magnesium chloride, 0.05% sodium azide, 109 U/liter ALP (obtained from human fetal hepatic cell strain BRL 68 by the same method as in the Reference Example 2), 61 U/liter CK (obtained from human promyeloid leukemia cell strain HL-60 by the same method as in the Reference Example 1), 38 U/liter AST (obtained from human promyeloid leukemia cell strain HL-60 by the same method as in the Reference Example 1), 34 U/liter ALT (hog heart-derived; manufactured and sold by Sigma Chemical Company, USA), 31 U/liter γ-GTP (bovine kidney-derived; manufactured and sold by Sigma Chemical Company, USA), and 103 U/liter LDH (obtained from human promyeloid leukemia cell strain HL-60 by the same method as in the Reference Example 1).

From the above enzyme compositions, the following samples were prepared:

(1) a sample which was prepared by adding trehalose to the above enzyme composition so that the sample had a trehalose concentration of 0.5%, (2) a sample which was prepared by adding trehalose to the above enzyme composition so that the sample had a trehalose concentration of 2%, (3) a sample which was prepared by adding trehalose to the above enzyme composition so that the sample had a trehalose concentration of 5%.

The residual enzymatic activity after the storage at 5° C. and −20° C. for 7 days was measured with respect to each of samples (1) to (3) to examine the influence of the concentration of trehalose on the enzymatic activity. The respective residual activities (%) of the enzymes after the storage at −20° C. for 7 days are shown in Table 5 and the respective residual activities (%) of the enzymes after the storage at 5° C. for 7 days are shown in Table 6.

TABLE 5

Residual activity (%) after storage at −20° C. for 7 days

|  |  | AST | ALT | γ-GTP | ALP | CK | LDH |
|---|---|---|---|---|---|---|---|
| Control | 0.5% Trehalose | 97 | 96 | 100 | 98 | 101 | 101 |
| Present invention | 2% Trehalose | 100 | 100 | 101 | 100 | 99 | 100 |
|  | 5% Trehalose | 100 | 99 | 101 | 100 | 100 | 100 |

TABLE 6

Residual activity (%) after storage at 5° C. for 7 days

|  |  | AST | ALT | γ-GTP | ALP | CK | LDH |
|---|---|---|---|---|---|---|---|
| Control | 0.5% Trehalose | 95 | 102 | 99 | 98 | 98 | 90 |
| Present invention | 2% Trehalose | 101 | 99 | 100 | 99 | 99 | 99 |
|  | 5% Trehalose | 102 | 98 | 100 | 98 | 99 | 101 |

As shown in Table 5, when the samples were stored at −20° C. for 7 days, any one of the enzyme components showed almost no lowering of the activity except that, with respect to sample (1) which had 0.5% trehalose added thereto, the activity of ALT was caused to a little lower as compared to the original activity. Whereas, as shown in Table 6, when the samples were stored at 5° C. for 7 days, the activity of LDH was caused to lower by 10% with respect to the sample (1) which had 0.5% trehalose added thereto, indicating that the above enzyme composition was not stabilized at 5° C. by adding trehalose in an amount of 0.5% or so. In this connection, it is to be noted that, in the case of the storage at 25° C. for 7 days, the activity of LDH was maintained at the original level at trehalose concentrations of 0.5%, 2% and 5%. It is suggested that LDH is unstable at lower temperatures. This inactivation of LDH at lower temperatures was not observed with respect to the samples respectively having 2% and 5% trehalose added thereto. The above shows that 2% or more trehalose is required to stabilize the above enzyme compositions.

EXAMPLE 5

Enzyme compositions of the following composition were provided:

20 mM PIPES-NaOH (pH 7.5),

3% BSA (manufactured and sold by Sigma Chemical Company, USA), 2 mM magnesium chloride, 0.05% sodium azide, 462 U/liter ALP (obtained from human fetal hepatic cell strain BRL 68 by the same method as in the Reference Example 2), 282 U/liter CK (obtained from human promyeloid leukemia cell strain HL-60 by the same method as in the Reference Example 1), 100 U/liter AST (obtained from human promyeloid leukemia cell strain HL-60 by the same method as in the Reference Example 1), 118 U/liter ALT (hog heart-derived; manufactured and sold by Sigma Chemical Company, USA), 146 U/liter γ-GTP (bovine kidney-derived; manufactured and sold by Sigma Chemical Company, USA), and 235 U/liter LDH (obtained from human promyeloid leukemia cell strain HL-60 by the same method as in the Reference Example 1).

From the above enzyme compositions, the following samples were prepared:

To the above-provided enzyme compositions were respectively added sorbitol, trehalose, mannitol and sucrose, each in a concentration of 5%.

The storage stability in a frozen form was examined after the storage at −20° C. The respective residual activities (t) of the enzymes after the storage at −20° C. for 9 months are shown in Table 7.

TABLE 7

Residual activity (%) after storage at −20° C. for 9 months

| | Controls | | Present invention | |
|---|---|---|---|---|
| | None | Mannitol | Sucrose | Sorbitol | Trehalose |
| AST | 92 | 98 | 98 | 101 | 102 |
| ALT | 66 | 90 | 96 | 100 | 102 |
| λ-GTP | 101 | 102 | 98 | 101 | 101 |
| ALP | 87 | 98 | 76 | 102 | 102 |
| CK | 95 | 91 | 97 | 100 | 100 |
| LDH | 94 | 101 | 97 | 102 | 102 |

As shown in Table 7, when the samples were stored at −20° C. for 9 months, with respect to the samples containing no saccharide, the respective activities of AST, ALT, ALP, CK and LDH were caused to lower by 8 to 34% as compared to the original activities. With respect to the samples having mannitol added thereto, the activities of ALT and CK were caused to lower by approximately 10% as compared to the original activities. With respect to the samples having sucrose added thereto, the respective activities of ALT, ALP and CK were caused to lower by 4 to 24% as compared to the original activities. By contrast, with respect to the samples respectively having sorbitol and trehalose added thereto, both of which are the stabilized enzyme compositions of the present invention, almost no lowering of the activity of each of the enzymes contained therein was observed.

Further, with respect to the above-mentioned samples respectively having sorbitol and trehalose added thereto, comparison was made between the residual activities of enzymes of a sample stored at 5° C. for 1 week after preparation thereof and those of a sample which was stored in a frozen form at −20° C. for 9 months and then subjected to thawing, followed by storage at 5° C. for 1 week after the thawing. The results are shown in Table 8.

TABLE 8

Residual activity (%) after storage at 5° C. for 7 days

| | A sample immediately after preparation | A sample thawed after the storage in a frozen form at −20° C. for 9 months | A sample immediately after preparation | A sample thawed after the storage in a frozen form at −20° C. for 9 months |
|---|---|---|---|---|
| AST | 100 | 99 | 100 | 100 |
| ALT | 99 | 99 | 99 | 99 |
| λ-GTP | 100 | 99 | 101 | 100 |
| ALP | 101 | 101 | 102 | 99 |
| CK | 99 | 98 | 99 | 100 |
| LDH | 100 | 101 | 101 | 100 |

As shown in Table 8, almost no difference in the residual activity was observed between the samples. immediately after preparation and the samples thawed after freezing. The samples which were thawed after the storage at −20° C. for 9 months were stable upon storage at 5° C. for 1 week, similarly to the samples immediately after preparation.

INDUSTRIAL APPLICABILITY

The enzyme composition of the present invention-comprising an enzyme component comprising at least two enzymes selected from the group consisting of alkaline phosphatase, creatine kinase and alanine aminotransferase; and a stabilizer component comprising effective stabilizing amounts of an albumin, and at least one saccharide selected from the group consisting of trehalose and sorbitol, shows almost no lowering of enzymatic activity, with respect to all enzymes contained therein, for at least one week when it is stored at 2 to 8° C. after preparation, for at least 15 months when it is frozen at −20° C. or lower, and for at least one week even when it is stored at 2 to 8° C. after thawing. This indicates that the enzyme composition of the present invention has extremely excellent storage stability. Therefore, the enzyme composition of the present invention can be advantageously used for the purpose of checking the precision in measurement, correcting measured values and calibrating the amount and activity of an enzyme, in a clinical examination for measuring the enzymatic activity in a sample, such as serum or the like.

What is claimed is:

1. A stabilized enzyme composition for use as a clinical diagnostic reagent, comprising:

(a) an enzyme component consisting essentially of a multiplicity of enzymes, said enzymes comprising alkaline phosphatase creatine kinase, alanine aminotransferase, aspartate aminotransferase, lactate dehydrogenase and γ-glutamyl transpeptidase;

(b) a stabilizer component in an amount sufficient to stabilize said enzyme component (a), wherein said stabilizer component comprises an albumin and sorbitol, wherein said sorbitol is at a concentration of 2–5% (w/v); and (c) an aqueous medium having dissolved therein said components (a) and (b).

2. The composition according to claim 1, wherein said alkaline phosphatase is present in a concentration of from 9 to 6500 U, said creatine kinase is present in a concentration of from 6 to 4000 U, said alanine aminotransferase is present in a concentration of from 3 to 1150 U, said aspartate aminotransferase is present in a concentration of from 3 to 1150 U, said lactate dehydrogenase is present in a concentration of from 8 to 4000 U, and said γ-glutamyl transpeptidase is present in a concentration of from 2 to 1200 U each per liter of said composition.

3. The composition according to claim 1, wherein, with respect to said stabilizer component (b), said albumin is present in a concentration of from 0.3 to 7 (w/v) %, based on the volume of said composition.

4. The composition according to claim 1, which is in a liquid form or in a frozen form.

5. The composition according to claim 1, wherein the enzymes of said enzyme component (a) are obtained from biological materials, derived from a human body, containing the enzymes; from cultures of cells, derived from human, capable of producing the enzymes; or from cultures of transformed cells, into which human genes coding for the enzymes have been integrated by gene recombination technique, capable of producing the enzymes.

6. The composition according to claim 5, which has a specific gravity of from 1.015 to 1.030 at 25° C., and a viscosity of from 1.05 to 1.40 cP at 37° C., each as directly measured when said composition is in a liquid form, or as measured after thawing said composition when said composition is in a frozen form.

* * * * *